United States Patent
Black et al.

(10) Patent No.: US 9,526,242 B2
(45) Date of Patent: *Dec. 27, 2016

(54) NEMATODE REPELLENT COMPOSITION

(71) Applicant: FMC Corporation, Philadelphia, PA (US)

(72) Inventors: Bruce C. Black, Yardley, PA (US); Linda Varanyak, Mercerville, NJ (US)

(73) Assignee: FMC Corporation, Philadelphia, PA (US)

( * ) Notice: Subject to any disclaimer, the term of this patent is extended or adjusted under 35 U.S.C. 154(b) by 2 days.

This patent is subject to a terminal disclaimer.

(21) Appl. No.: 14/333,926

(22) Filed: Jul. 17, 2014

(65) Prior Publication Data

US 2015/0025140 A1     Jan. 22, 2015

Related U.S. Application Data

(60) Provisional application No. 61/847,805, filed on Jul. 18, 2013, provisional application No. 62/001,758, filed on May 22, 2014.

(51) Int. Cl.
*A01N 37/10* (2006.01)
*A01N 37/44* (2006.01)

(52) U.S. Cl.
CPC ..................... *A01N 37/44* (2013.01)

(58) Field of Classification Search
CPC ...................................... A01N 37/44
USPC ....................................... 514/537
See application file for complete search history.

(56) References Cited

U.S. PATENT DOCUMENTS

| | | | |
|---|---|---|---|
| 2,967,128 A | 1/1961 | Kare | |
| 5,175,175 A | 12/1992 | Wilson et al. | |
| 5,296,226 A | 3/1994 | Askham | |
| 5,662,914 A | 9/1997 | Shorey et al. | |
| 6,124,359 A * | 9/2000 | Feitelson et al. | 514/552 |
| 6,780,885 B1 * | 8/2004 | Campbell et al. | 514/424 |
| 6,958,146 B2 | 10/2005 | Askham et al. | |
| 7,867,479 B2 | 1/2011 | Dunham et al. | |
| 8,092,790 B2 | 1/2012 | Dunham et al. | |
| 2004/0242699 A1 * | 12/2004 | Askham et al. | 514/619 |
| 2015/0025141 A1 * | 1/2015 | Black et al. | 514/537 |

FOREIGN PATENT DOCUMENTS

| | | |
|---|---|---|
| CA | 2513269 A1 | 8/2004 |
| EP | 0828328 A2 | 3/1998 |

OTHER PUBLICATIONS

Rollo C.D. et al., "Fatty Acid Necromones for Cockroaches" Naturwissenschaften 81, pp. 409-410 (1994).
Appel, Arthur G, et al., Factors Affecting Coprophagy and Necrophagy by the German Cockroach (Dictyoptera: Blattellidae), Proceedings of the Sixth International Conference on Urban Pests, (2008), pp. 139-142.
Bird Shield® Repellent Concentrate Label, Bird Shield Corporation, Pullman, WA 99163, www.birdshield.com, 6 pages.
Colby S.R. "Calculating Synergistic and Antagonistic Responses of Herbicide Combinations" Weeds, 1967, 15, pp. 20-22.

* cited by examiner

*Primary Examiner* — T. Victor Oh
(74) *Attorney, Agent, or Firm* — FMC Corporation

(57) ABSTRACT

In one aspect, this invention relates to a nematode repellent composition comprising an effective nematode repellent amount of a fatty acid and an anthranilate ester. In another aspect, this invention relates to a method of repelling nematodes employing such composition.

25 Claims, No Drawings

NEMATODE REPELLENT COMPOSITION

FIELD OF THE INVENTION

In one aspect, this invention relates to a nematode repellent composition comprising an effective nematode repellent amount of a fatty acid and an anthranilate ester. In another aspect, this invention relates to a method of repelling nematodes employing such composition.

BACKGROUND OF THE INVENTION

Plant parasitic nematodes cause billions of dollars of damage each year to agronomic crops, vegetables, fruits, flowering trees and shrubs. Almost all major plant species are susceptible to infection by these pests, which typically affect the roots of host plants but also can damage aboveground parts including the stem, leaves and flowers. Nematodes of particular concern include those belonging to the genera *Meloidogyne* (root knot), *Heterodera* (cyst), *Globodera* (cyst), *Pratylenchus* and *Xiphinema*.

Accordingly there is a need for a means to reduce the damage caused by nematodes. In the past, most attempts at nematode control have involved the application of chemical nematicides and/or of organisms such as certain fungi and bacteria which have similarly been found to exhibit control by killing nematodes. Unfortunately, due to their toxicity, many effective chemical nematicides have come under scrutiny from the Environmental Protection Agency (EPA) and other regulatory agencies. As a result, the use of many traditional chemical nematicides such as methyl-bromide and organophosphates has been phased out, creating a need for the development of alternative treatments for nematodes.

In this regard, it would be desirable to possess a nematode treatment which acted by a different mode of action, such that such treatment could be used in a complimentary manner with known chemical and/or biological nematicides.

Anthranilate esters such as methyl anthranilate and dimethyl anthranilate have long been known to be useful as bird repellents. Thus, U.S. Pat. No. 2,967,128 (Kare) describes the use of such compounds to deter both domestic and wild birds from eating seeds, berries, grains, fruits and the like. A formulation of dimethyl anthranilate has been commercialized as the product BIRDSHIELD™. As is detailed in U.S. Pat. No. 5,296,226 this bird repellent composition comprises an anthranilate ester and an alkyl metal salt of a fatty acid; rather than a fatty acid in acid form. According to this publication, the addition of such fatty acid salts results in the formation of micelles of such anthranilate compounds, permitting a more even distribution of such compounds on the surface treated and enhancing their efficacy as bird repellents.

Further, anthranilate esters have been identified as being insect attractants—for example, U.S. Pat. No. 5,296,226 (Askham) states (at Column 3, lines 20-23) that "insects are readily attracted to dimethyl and methyl anthanilate. Crops relatively free of insects were quickly reinfested after being treated with either material." This finding is supported by the disclosures in U.S. Pat. No. 6,958,146 (Askham et al), U.S. Pat. No. 7,867,479 (Dunham et al) and U.S. Pat. No. 8,092,790 (Dunham et al) which show in Table 1 of such publications that sticky traps containing methyl anthranilate quickly became covered with hundreds of insects. The sole exception presented in these patents are house flies (*Musca domesticae*) which are repelled by the use of methyl anthranilate.

Rollo et al, "Fatty Acid Necromones for Cockroaches", Naturwissenschaften 81, 409-410 (1994) discloses that certain fatty acids (steric acid, oleic acid and linoleic acid) produced in dead cockroaches function as necromones which will repel live cockroaches; while other fatty acids (palmitic acid) similarly produced do not exhibit such a repellency effect. However, the efficacy of such necromones as commercial cockroach repellents is questionable, given that cockroaches will engage in necrophagy (the consumption of corpses) if other food sources are not available—see, for example, Appel et al, *Factors Affecting Corpophagy and Necrophagy by the German Cockroach*, Proceedings of the Sixth International Conference on Urban Pests (2008).

While such art discusses the attractant/repellent effects of anthranilates (and related compounds) and/or fatty acids (and related compounds) on insects and birds, none of such publications discuss applying such materials to nematode infested soil. Consequently, it could not have been predicted that a composition comprising an anthranilate ester and a fatty acid will effectively repel nematodes.

SUMMARY OF THE INVENTION

In one aspect, the present invention is directed to a composition comprising an effective nematode repellant amount of a composition comprising: (a) an anthranilate ester; and (b) a fatty acid. In another aspect this invention is directed to a method of repelling nematodes employing such composition.

DETAILED DESCRIPTION OF THE INVENTION

In one aspect, the present invention is directed to a composition comprising an effective nematode repellant amount of a composition comprising: (a) an anthranilate ester; and (b) a fatty acid.

The anthranilate esters which may be employed include those compounds described in U.S. Pat. No. 2,967,128, which publication is hereby incorporated by reference, and include dimethyl anthranilate, methyl anthranilate, ethyl anthranilate, phenylethyl anthranilate and menthyl anthranilate. Preferred anthranilate esters are dimethyl anthranilate and methyl anthranilate, with methyl anthranilate being particularly preferred.

The fatty acids which may be employed as component (b) include saturated and unsaturated fatty acids containing from 8 to 24 carbon atoms, with fatty acids containing from 13 to 21 carbon atoms being preferred. Illustrative of the fatty acids which may be employed are oleic acid, ricinoleic acid, linoleic acid palmitic acid and stearic acid; with oleic acid being particularly preferred.

The fatty acids may be employed in the form of their salts or esters. When employed as salts, the use of postassium and/or sodium salts is typically preferred. Esters which may be employed include $C_1$-$C_5$ alkyl esters, with ethyl esters being particularly preferred.

Typically, the weight ratio of fatty acid to anthranilate ester employed in the compositions of the present invention range from 1:10 to 20:1. Preferably, such ratio will range from 1:5 to 10:1; more preferably such ratio is from 1:1 to 5:1.

The compositions of this invention may further comprise additional additives conventionally employed in agricultural applications. Illustrative of further components which may be included in the compositions of this invention are antioxidant agents which serve to substantially prolong the desirable action of the fatty acid. Such antioxidant agent(s) protect the chemical and physical integrity of the fatty acid against reaction with oxygen and air pollution alone or in the presence of light. There exists an abundance of suitable antioxidants including commercial and specialty chemicals and their combinations, mixtures and proprietary compositions that are well known to those educated in the art. One particular antioxidant agent is ascorbic acid palmitate. The amount of the antioxidant is preferably from 0.001-0.1% by weight of the total composition.

In certain embodiments, the compositions of this invention further comprise one or more nematicidal agents selected from the group consisting of chemical nematicides, biological nematicides and nematicidal agents of natural origin.

Chemical nematicides which may be employed include antibiotic nematicides such as abamectin; carbamate nematicides such as benomyl, carbofuran, carbosulfan, and cleothocard; oxime carbamate nematicides such as alanycarb, aldicarb, aldoxycarb, oxamyl; organophosphorous nematicides such as diamidafos, fenamiphos, fosthietan, phosphamidon, cadusafos, chlorpyrifos, dichlofenthion, dimethoate, ethoprophos, fensulfothion, fosthiazate, heterophos, isamidofos, isazofos, methomyl, phorate, phosphocarb, terbufos, thiodicarb, thionazin, triazophos, imicyafos, and mecarphon. In addition, other compounds with nematicidal activity which may be employed include acetoprole, benclothiaz, chloropicrin, dazomet, dichlorophenolindophenol, 1,2-dichloropropane, 1,3-dichloropropene, furfural, iodomethane, metam, methyl bromide, methyl isothiocyanate, and xylenols.

Biological nematicides which may be employed include *Myrothecium verrucaria*, *Burholderia cepacia*, *Bacillus chitonosporus* and *Paecilomyces lilacinus*. Nematicidal agents of natural origin which may be employed include hairpin proteins, amino acid sequences or virus and viroid particles.

While the composition of this invention can be used neat, i.e. undiluted, it is preferably employed in diluted form. For example, the composition can be dissolved in a suitable solvent, such as a $C_1$-$C_4$ alcohol (for example, methanol, ethanol, isopropyl alcohol, butanol), a ketone such as acetone, an ester such as ethyl acetate or isopropyl myristate, a refined petroleum distillate solution (for example Sunspray® 6E from Sunoco Inc.) or other non-reactive solvent that will evaporate, preferably in a short period of time, leaving the active mixture of fatty acid and anthranilate ester. Typically, such composition will comprise between 0.1% and 60% by weight of anthranilate ester plus fatty acid; preferably, such composition will comprise between 0.4% and 40% by weight of such compounds.

The composition can be formulated with adjuvants, surfactants, stabilizers and preservatives, to be diluted with water for spray, seed treatment or other application.

The method of this invention comprises applying an effective nematode repellent amount of the composition of this invention to a locus where such repelling is desired. In this regard, such composition is typically employed as a seed treatment or applied in furrow during planting employing processes well known to those of skill in the art.

The composition of this invention is employed in a concentration sufficient to repel nematodes. Typically, the composition will be employed in a concentration of at least 100 ppm by weight of anthranilate ester plus fatty acid. Preferably, the composition is employed in a concentration of at least 500 ppm by weight of anthranilate ester plus fatty acid; and more preferably in a concentration of at least 1000 ppm by weight of anthranilate ester plus fatty acid. The upper limit of application is not particularly important from an efficacy point of view, but is limited by economic and physical factors.

EXAMPLES

The following examples are provided to illustrate the invention in accordance with the principles of this invention, but are not to be construed as limiting the invention in any way except as indicated in the appended claims.

Example 1

A plant tray having 32 wells was reconstructed using tape to form 16 test arenas each composed of two wells connected by a concave dip. The bottom of each well was lined with aluminum foil to prevent water and/or the treatment composition from escaping. One well in each such test arena was filled with untreated soil while the other well was filled with soil that had been treated with an emulsifiable concentrate comprised of 30% oleic acid ("OA"), 10% methyl anthranilate ("MA"), 52% methyl laurate, 4% Agnique® ABS 60CB (Calcium Dodecyl Benzene Sulfonate from Cognis Corporation), 2% Agnique® CDS-40 and 2% Tergitol XD at the rates set forth in Table 1 below. As a control a formulation without oleic acid and methyl anthranilate was tested.

The soil in both wells was treated to a 9% moisture level and Tiny Tim tomato plants transplanted to the wells. The tray was placed in a head house and allowed to acclimate overnight. It was observed that the plants had wilted, so they were watered heavily and placed into a growth chamber overnight to restore them. Two days after being transplanted, a nematode inoculum of *Meloidogyne* spp. (180 J2 larva/pot) was placed into a dip connecting the two pots. The plants were grown in a growth chamber for one month at 25° C. After this interval, soil was washed from the roots and the number of galls on each tomato plant was recorded. The results of such testing are summarized in Table 1 below:

TABLE 1

| Concentration (OA + MA) ppm | Percentage of Galls in Plants in Treated Soil | Percentage of Galls in Plants in Untreated Soil |
|---|---|---|
| 1000 | 6.4 | 93.6 |
| 100 | 53.8 | 46.2 |
| 10 | 30.9 | 69.1 |
| Control (0) | 44.7 | 55.3 |

Data for 10 and 1000 average of 2 replicates; data for 100 and control average of 3 replicates.

Example 2

Employing the apparatus, formulation and methodology described in Example 1, an additional evaluation was run as per protocol except that the soil was moistened to 12% and the nematode inoculum was added the day after replanting. The results of such testing are summarized in Table 2 below:

TABLE 2

| Concentration (OA + MA) ppm | Percentage of Galls in Plants in Treated Soil | Percentage of Galls in Plants in Untreated Soil |
|---|---|---|
| 1000 | 25.8 | 74.2 |
| 100 | 38.5 | 61.5 |
| 10 | 46.0 | 54.0 |
| Control (0) | 47.5 | 52.5 |

All data is the average of 4 replicates.

The above results indicate that the composition of the present invention is effective in repelling nematodes.

What is claimed is:

1. A composition suitable for repelling nematodes, the composition comprising a nematode repellant composition consisting essentially of: (a) an anthranilate ester; and (b) at least one of a fatty acid and a fatty acid ester;
wherein the weight ratio of component (b) to anthranilate ester is in a range of from about 1:10 to about 20:1.

2. The composition of claim 1 wherein component (b) of the nematode repellant composition further comprises a fatty acid salt.

3. The composition of claim 1, wherein said anthranilate ester is selected from the group consisting of dimethyl anthranilate, methyl anthranilate, ethyl anthranilate, phenylethyl anthranilate and menthyl anthranilate.

4. The composition of claim 1, wherein said anthranilate ester is methyl anthranilate or dimethyl anthranilate.

5. The composition of claim 1, wherein said fatty acid is selected from the group consisting of saturated and unsaturated fatty acids containing from 8 to 24 carbon atoms.

6. The composition of claim 1, wherein said fatty acid is selected from the group consisting of oleic acid, ricinoleic acid, linoleic acid, palmitic acid and stearic acid.

7. The composition of claim 1, wherein the fatty acid is oleic acid.

8. The composition of claim 2 wherein the fatty acid salt is a sodium or potassium salt.

9. The composition of claim 1, wherein component (b) comprises a $C_1$-$C_5$ fatty acid alkyl ester.

10. The composition of claim 9, wherein the fatty acid alkyl ester is an ethyl ester.

11. The composition of claim 1 wherein the weight ratio of component (b) to anthranilate ester is from 1:5 to 10:1.

12. The composition of claim 1, wherein the weight ratio of component (b) to anthranilate ester is from 1:1 to 5:1.

13. The composition of claim 1, wherein the composition further comprises a solvent.

14. The composition of claim 13, wherein the anthranilate ester and component (b) comprise between 0.1% and 60% by weight of the composition.

15. The composition of claim 14, wherein the anthranilate ester and component (b) comprise between 0.4% and 40% by weight of the composition.

16. The composition of claim 13, wherein the solvent is selected from the group consisting of $C_1$-$C_4$ alcohols, esters, ketones, petroleum distillates, glycols, and mixtures of two or more thereof.

17. The composition of claim 1, wherein the composition further comprises an antioxidant preservative agent.

18. The composition of claim 1, wherein said composition further comprises one or more nematicidal agents selected from the group consisting of chemical nematicides, biological nematicides, hairpin proteins, amino acids, viruses and viroid particles.

19. A method of repelling nematodes comprising the step: applying to a locus where such repelling is desired, a nematode-repelling effective amount of a nematode repellant composition comprising: (a) an anthranilate ester; and (b) at least one of a fatty acid, a fatty acid ester, or a mixture of these wherein the weight ratio of component (b) to anthranilate ester is in a range of from about 1:10 to about 20:1.

20. The method of claim 19, wherein the composition contains a concentration of at least 100 ppm by weight of anthranilate ester plus fatty acid.

21. The method of claim 20 wherein the composition contains a concentration of at least 500 ppm by weight of anthranilate ester plus fatty acid.

22. The method of claim 21 wherein the composition contains a concentration of at least 1000 ppm by weight of anthranilate ester plus fatty acid.

23. The method of claim 19, wherein the composition is applied as a seed treatment.

24. The method of claim 19, wherein the composition is applied in furrow.

25. The method of claim 19, wherein the nematode is at least one belonging to the genera selected from the group consisting of: *Meloidogyne; Heterodera; Globodera; Pratylenchus*; and *Xiphinema*.

* * * * *